(12) United States Patent
Nierich (10) Patent No.: US 11,311,273 B2
(45) Date of Patent: Apr. 26, 2022

(54) SYSTEM WITH AN INFLATABLE MEMBER FOR BEING ARRANGED IN THE PATIENT'S RESPIRATORY TRACT

(71) Applicant: Stroke2Prevent BV, Zwolle (NL)

(72) Inventor: Arno Nierich, Hattem (NL)

(73) Assignee: STROKE2PREVENT BV, Zwolle (NL)

( * ) Notice: Subject to any disclaimer, the term of this patent is extended or adjusted under 35 U.S.C. 154(b) by 357 days.

(21) Appl. No.: 16/467,099

(22) PCT Filed: Dec. 4, 2017

(86) PCT No.: PCT/NL2017/050805
§ 371 (c)(1),
(2) Date: Jun. 6, 2019

(87) PCT Pub. No.: WO2018/106103
PCT Pub. Date: Jun. 14, 2018

(65) Prior Publication Data
US 2019/0321001 A1 Oct. 24, 2019

(30) Foreign Application Priority Data
Dec. 9, 2016 (NL) ..................................... 2017970

(51) Int. Cl.
*A61B 8/00* (2006.01)
*A61M 25/10* (2013.01)
(Continued)

(52) U.S. Cl.
CPC ................ *A61B 8/445* (2013.01); *A61B 8/12* (2013.01); *A61B 8/4281* (2013.01);
(Continued)

(58) Field of Classification Search
CPC ......... A61B 8/445; A61B 8/12; A61B 8/4281; A61B 8/0883; A61M 25/10187; A61M 25/0102; A61M 2205/3382
See application file for complete search history.

(56) References Cited

U.S. PATENT DOCUMENTS 5,049,130 A 9/1991 Powell
8,500,688 B2 * 8/2013 Engel .................... A61L 29/126
604/103.08
(Continued)

FOREIGN PATENT DOCUMENTS

CN 102119038 A 7/2011
CN 105682552 A 6/2016
(Continued)

OTHER PUBLICATIONS

International Search Report and Written Opinion for the International Patent Application No. PCT/NL2017/050805, dated Feb. 13, 2018, 11 pages.

*Primary Examiner* — Joel Lamprecht
(74) *Attorney, Agent, or Firm* — Kacvinsky Daisak Bluni PLLC (57) ABSTRACT

A system with at least one inflatable member configured for being arranged in a part of the patient's respiratory tract includes a catheter carrying the at least one inflatable member. The catheter includes a fluid line for filling the inflatable member with a fluid; and a pressure monitoring and control member to be arranged outside the patient's body. The pressure monitoring member is in fluid communication with the inflatable member and is configured to receive, during operation, fluid from the inflatable member when the pressure increases above a predetermined threshold pressure and to return the received fluid when the pressure decreases below said predetermined threshold pressure. The pressure monitoring and control member is an (Continued)

elastically expandable balloon made from a material configured to expand elastically when the pressure in the balloon increases above a predetermined threshold pressure and to contract when the pressure decreases below said predetermined threshold pressure.

20 Claims, 5 Drawing Sheets

(51) Int. Cl.
  *A61B 8/12*   (2006.01)
  *A61B 8/08*   (2006.01)
  *A61M 25/01*   (2006.01)

(52) U.S. Cl.
  CPC ...... *A61M 25/10187* (2013.11); *A61B 8/0883* (2013.01); *A61M 25/0102* (2013.01); *A61M 2205/3382* (2013.01)

(56) References Cited

U.S. PATENT DOCUMENTS

| | | |
|---|---|---|
| 10,952,676 B2 * | 3/2021 | Babkin .................. A61B 8/12 |
| 2010/0268159 A1 | 10/2010 | Engel et al. |
| 2011/0125026 A1 | 5/2011 | Neto |
| 2013/0345552 A1 | 12/2013 | Arts et al. |
| 2016/0022943 A1 | 1/2016 | Kanowitz |
| 2016/0249859 A1 | 9/2016 | Babkin et al. |
| 2016/0354144 A1 * | 12/2016 | Caplan ............... A61B 18/1492 |

FOREIGN PATENT DOCUMENTS

| | | |
|---|---|---|
| EP | 1034743 A1 | 9/2000 |
| WO | 9964099 A1 | 12/1999 |

* cited by examiner

SYSTEM WITH AN INFLATABLE MEMBER FOR BEING ARRANGED IN THE PATIENT'S RESPIRATORY TRACT

This is a national stage application filed under 35 U.S.C. § 371 of pending international application PCT/NL2017/050805 filed Dec. 4, 2017, which claims priority to Netherlands Patent application NL 2017970, filed Dec. 9, 2016, the entirety of which applications are hereby incorporated by reference herein.

TECHNICAL FIELD

The present invention relates to a system with an inflatable member configured for being arranged in a part of the patient's respiratory tract.

BACKGROUND OF THE INVENTION

Transesophageal echocardiography (TEE) is an ultrasonic imaging method widely used imaging technique for evaluating cardiac structure, function, and valvular anatomy. TEE has also provided a new perspective on the thoracic aorta, and there is growing evidence that the technique contributes valuable and sometimes unique information about aortic structure and pathology.

TEE involves introducing an echo probe into the patient's esophagus and transmitting ultrasound waves across the thorax in the direction of the heart and aorta. However, visualization of the ascending aorta by internal TEE is limited by an air structure, i.e. the trachea and main left and right bronchi. This is due to an important physical limitation of ultrasound: absorption of ultrasound waves. This absorption is dependent of the medium and expressed in terms of the "half power distance": the distance in which half of the ultrasound energy will be absorbed. For water this is 360 cm, bone 0.2 cm and for air 0.06 cm. This means that in practice ultrasound waves will not travel through bone or air. Unfortunately, by the anatomical location of the distal aorta ascendens, the arch and the upper part of the main vascular side branches, it is difficult to view this area by TEE because the view is obstructed by the trachea. The trachea is located between the esophagus and the vascular tree, so all echoes are reflected by the trachea, which is filled with air.

In order to solve this problem, WO 00/53098 in the name of the Applicant proposes the use of an inflatable member that may be arranged in the trachea or in one of the bronchi and that may be filled with an ultrasonic transmission fluid, e.g. water or a saline solution in minor concentrations. Obviously, this can only be done during operative surgery, when the patient is mechanically ventilated or on cardiopulmonary bypass, since in order to be effective the balloon has to completely filled with saline and will block the trachea or bronchus. U.S. Pat. No. 8,936,554 also in the name of the Applicant discloses a further improved method and system for ultrasonic imaging using improved positioning means for positioning the inflatable member at a predetermined location in the tract.

SUMMARY OF THE INVENTION

A problem which arises when performing the TEE assisted by an inflatable member placed in the respiratory tract, is that the indirect contact between the TEE probe and the inflatable member via the esophagus and trachea walls, especially during the movement of the TEE probe in the esophagus, causes a large increase in pressure within the inflatable member. This pressure increase increases the pressure applied to the trachea wall. If the pressure applied to the trachea wall is too much, it causes potential tissue damage to the trachea. Also in other applications where a device is manipulated close to an inflatable member placed in the respiratory tract, a pressure increase within the inflatable member may lead to damage of the trachea.

The object of embodiments of the invention is to provide a system with an inflatable member for positioning in a part of the patient's respiratory tract which allows for an improved pressure control such that damage can be avoided.

According to a first aspect there is provided a system with at least one inflatable member configured for being arranged in a part of the patient's respiratory tract. The system comprises a catheter, and a pressure monitoring and control member. The catheter carries the at least one inflatable member to be arranged in the respiratory tract, and comprises a fluid line for filling the inflatable member with a fluid. The pressure monitoring and control member intends to be arranged outside the patient's body. The pressure monitoring and control member is in fluid communication with the inflatable member and being configured to receive, during operation, fluid from the inflatable member when the pressure increases above a predetermined threshold pressure and to return said received fluid when the pressure decreases below said predetermined threshold pressure. The pressure monitoring and control member is an elastically expandable balloon made from a material which is configured to expand elastically when the pressure in the balloon increases above a predetermined threshold pressure and to contract when the pressure decreases below said predetermined threshold pressure.

Embodiments of the invention are based inter alia on the inventive insight that in case of an increase of pressure inside the inflatable member arranged in the respiratory tract, above a predetermined threshold pressure, the elastically expandable balloon will expand rather than the inflatable member. The balloon is located outside the patient, and the increase in volume thereof will limit the pressure increase within the inflatable member, resulting in no or less damage to the trachea wall.

Preferably, the elastically expandable balloon and the inflatable member are configured such that, when there is exerted a pressure against the inflatable member, when positioned in the respiratory tract and filled with fluid, fluid is displaced from the inflatable member to the expandable balloon. In other words, the expendable balloon should be sufficiently flexible to allow expansion in case of pressure on the internal balloon.

According to an exemplary embodiment, the system further comprises an imaging device, preferably an ultrasonic imaging device, configured to be arranged in or on the patient's body; wherein said fluid is an imaging liquid. The above system enables the transmission of the ultrasound waves through the imaging liquid in the inflatable member without absorption by the air in the respiratory tract, and enables a safe evaluating of an organ in a patient's body by ultrasound.

According to another exemplary embodiment, the volume of the elastically expandable balloon, in the non-expanded state, is at least 10 percent of the volume of the inflatable member. In this way the volume of the elastically expandable balloon may be large enough to absorb the influx of excessive fluid coming from the inflatable member in case of increasing pressure within the respiratory tract.

According to yet another exemplary embodiment, the material of the elastically expandable balloon is a thermoplastic elastomer, preferably a thermoplastic polyurethane elastomer, e.g. Pellethane 2363-80A.

Preferably the tensile modulus of the material of the elastically expandable balloon is as follows, wherein the ASTM D412 test method is used:

50% Elongation: between 2 and 6 MPa
100% Elongation: between 4 and 9 MPa
300% Elongation: between 8 and 16 MPa.

Preferably, the durometer hardness of the material of the elastically expandable balloon, using test method ASTM D2240, is between 75A and 85A Shore.

Preferably the durometer hardness of the material of the elastically expandable balloon, using test method ASTM D2240, is lower than the durometer hardness of the material of the inflatable member, more preferably at least 2A Shore lower, most preferably at least 5A Shore lower.

Preferably the tensile modulus of the material of the elastically expandable balloon, wherein the ASTM D412 test method is used, is lower than the tensile modulus of the material of the inflatable member, more preferably at least 1 MPa lower at 50% elongation, and at least 2 MPa lower at 100% elongation.

According to a further developed embodiment, the predetermined threshold pressure of the system lies in a range between 30 and 70 mm Hg. The elastically expandable balloon will expand when the pressure exceeds the predetermined threshold, thereby buffering the pressure increase in the inflatable member within the respiratory tract, so that damage to the trachea wall can be avoided.

According to a further developed embodiment, the volume of the elastically expandable balloon, in the non-expanded state, is between 2 and 10 ml, preferably between 2.5 and 6 ml, so that volume of the elastically expandable balloon may be large enough to absorb the influx of excessive imaging fluid coming from the inflatable member in case of increasing pressure within the respiratory tract.

According to yet another exemplary embodiment, the expansion of the elastically expandable balloon, when the pressure is above the predetermined threshold pressure is essentially linear with respect to the pressure, so that the pressure within the inflatable member can be monitored by measuring the size of the expandable balloon.

According to yet another exemplary embodiment, the material of the inflatable member is a thermoplastic polyurethane elastomer, e.g. Pellethane 2363-90AE.

Preferably the tensile modulus of the material of the inflatable member is as follows, wherein the ASTM D412 test method is used:

50% Elongation: between 5 and 9 MPa
100% Elongation: between 7 and 13 MPa
300% Elongation: between 15 and 25 MPa.

Preferably the durometer hardness of the material of the inflatable member, using test method ASTM D2240, is between 85A and 95A shore.

According to yet another exemplary embodiment, wherein the inflatable member, in the non-expanded state, has a volume between 20 ml and 60 ml, preferably between 30 ml and 50 ml, so that it enables the filling of a substantial portion of the respiratory tract.

According to yet another exemplary embodiment, the system further comprises positioning means for positioning the inflatable member at a predetermined location in the respiratory tract, so that the imaging examination can be performed at the right anatomical locations. The positioning means may comprise guide means that are attached to or integrated with the flexible catheter. These guide means allow the inflatable member carried by catheter to be swiftly and easily guided to its predetermined position. Preferably, the guide means comprises a stylet arranged in the catheter and having a distal end at a tip of the catheter, said stylet extending beyond the inflatable member.

According to yet another exemplary embodiment, the elastically expandable balloon of the system has a thickness between 0.01 mm and 0.1 mm, preferably between 0.03 mm and 0.07 mm.

According to yet another exemplary embodiment, the system further comprises a breathing tube having a first end and a second end. The first end of the trachea tube is adapted for connection to a source of respiratory gas, and the second end is adjacent to and surrounded by the inflatable member. In this way during mechanical ventilation of the patient through the breathing tube, the system forms a gas tight seal against the tracheal wall and prevents aspiration of secretion, meanwhile preventing damage to the tracheal wall when the breathing tube is manipulated. Indeed, manipulating the breathing tube may cause a pressure increase in the inflatable member but this pressure increase will cause the elastically expandable balloon located outside the patient's body to expand avoiding that a high pressure is exerted on the wall of the respiratory tract.

BRIEF DESCRIPTION OF THE DRAWINGS

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

DESCRIPTION OF THE PREFERRED EMBODIMENTS

For purposes of the description hereinafter, the terms "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

It is to be understood that the invention may assume various alternative variations and step sequences, except where expressly specified to the contrary. It is also to be understood that the specific devices and processes illustrated in the attached drawings, and described in the following specification, are simply exemplary embodiments of the invention.

In the first shown exemplary embodiment (FIG. 1), the system comprises at least one inflatable member 7 carried by a flexible catheter 6. For instance in the actual practice of ultrasonic imaging, the flexible catheter 6 carrying the inflatable member 7 will be guided through the patient's trachea into the right position, e.g. patient's left main bronchus. In this embodiment, the guide means include a short stylet 11, which may be arranged between the inflatable member 7 and the distal end of the catheter 6. Positioning of the catheter 6 and the inflatable member 7 is done by manipulating the proximal end of the catheter 6. The presence of the stylet 11 adds stiffness to the distal end of the flexible catheter 6, improving directional control and predictability of the movement, thereby it allows the inflatable member 7 to be swiftly and accurately positioned in the respiratory tract. Such short stylet has an additional advantage that it does extend across the inflatable member 7, so that it will not interfere with the travel of ultrasonic waves and there is no need to retract it before imaging.

Figure 1:
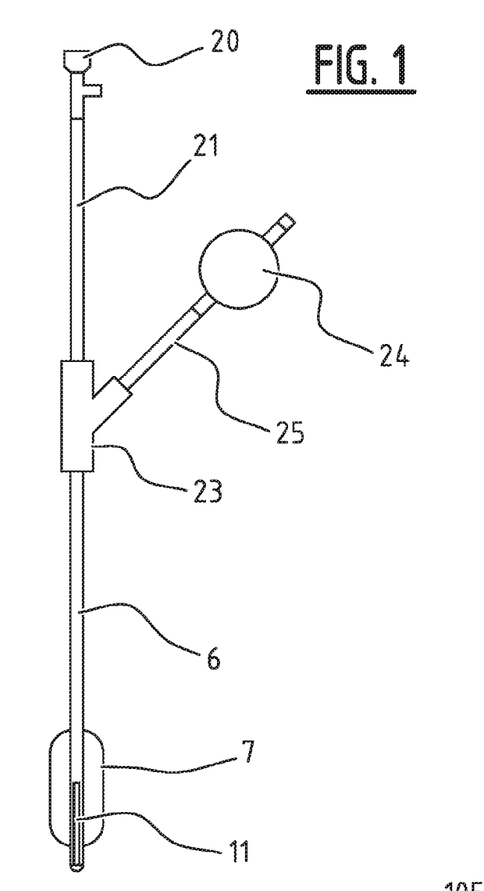
FIG. 1 is a schematic view of an exemplary embodiment of the system of the invention, including an elastically expandable balloon connected to the inflatable member.

After the inflatable member 7 has been positioned at the right position in the respiratory tract, it is filled with a fluid, e.g. water or a saline solution in minor concentrations, through the flexible catheter 6. The inflatable member 7, in the non-expanded state, has a volume between 30 ml and 70 ml, preferably between 40 ml and 60 ml. The fluid is injected into the catheter 6 by means of a syringe (not shown), which is connected to a fill connector 20 at the proximal end of a fill line 21. The distal end of this fill line 21 in turn is connected to a proximal end of the catheter 6 through a connector 23. The degree of filling of the inflatable member 7 may be visually determined by monitoring an elastically expandable balloon 24, which is arranged at the end of a pilot line 25. This pilot line 25 is also connected to the catheter 6 through the connector 23. In case of an increasing pressure within the inflatable member 7 exceeding the threshold level, e.g. during the movement of echo probe in the oesophagus or the movement breathing tube in the respiratory tract, the pressure may cause a reflux of the fluid from the inflatable member 7 to the elastically expandable balloon 24. Such reflux may lead to an expansion of the elastically expandable balloon 24, thereby limiting the pressure increase within the inflatable member to a safety level. The predetermined threshold pressure of the system lies in a range between 30 and 90 mm Hg, such threshold pressure ensures a safe pressure within the inflatable member leading to no or less damage to the trachea wall.

Figure 2:
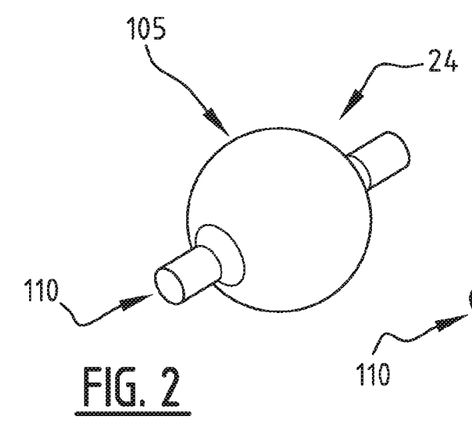
FIG. 2 is a detailed view of a first embodiment of the elastically expandable balloon.
Figure 3:
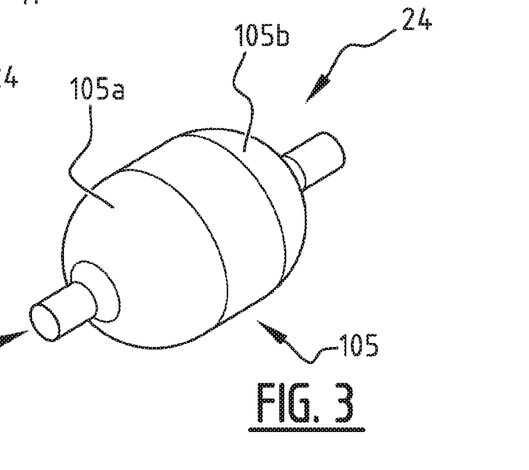
FIG. 3 is a detailed view of a second embodiment of the elastically expandable balloon.

In a first embodiment the elastically expandable balloon 24 has a main body 105 with a sphere shape (FIG. 2). In an alternative embodiment the elastically expandable balloon 24 has a main body 105 of a cylindrical shape, in between two semi-spherical ends 105a, 105b (FIG. 3). In the embodiments of FIGS. 2 and 3 the elastically expandable balloon 24 has one open tube end 110 connected to on one side of the main body 105 of the balloon 24. The open tube end 110 can be connected to the end of a pilot line 25 such that fluid can flow from the pilot line 25 to the expandable balloon 24. Preferably the tube end 110 is integrally made with the main body 105 of the balloon 24. Optionally the other side of the main body 105 of the balloon 24 also has an open tube end 120. Preferably, the volume of the elastically expandable balloon 24, in the non-expanded state, is at least 10 percent of the volume of the inflatable member 7, preferably between 2 and 10 ml, more preferably between 2.5 and 6 ml. In this way the volume of the elastically expandable balloon 24 may be large enough to absorb the influx of excessive fluid coming from the inflatable member in case of increasing pressure within the respiratory tract. Preferably, the material of the inflatable member 7 is a thermoplastic elastomer, more preferably a thermoplastic polyurethane elastomer, e.g. Pellethane 2363-90AE. Preferably, the material of the elastically expandable balloon 24 is a thermoplastic elastomer, preferably a thermoplastic polyurethane elastomer, e.g. Pellethane 2363-80A. Preferably, the wall of the expandable balloon 24, in the non-expanded state, has a thickness between 0.01 mm and 0.1 mm, preferably between 0.03 mm and 0.07 mm. The expansion of the elastically expandable balloon 24, when the pressure is above the predetermined threshold pressure, may be essentially linear with respect to the pressure, so that the pressure within the inflatable member 7 can be monitored by measuring the size, e.g. the perimeter, of the expandable balloon 24.

There are various possibilities for guiding the catheter 6 carrying the inflatable member 7 to the predetermined position in e.g. the left bronchus 8.

Figure 4:
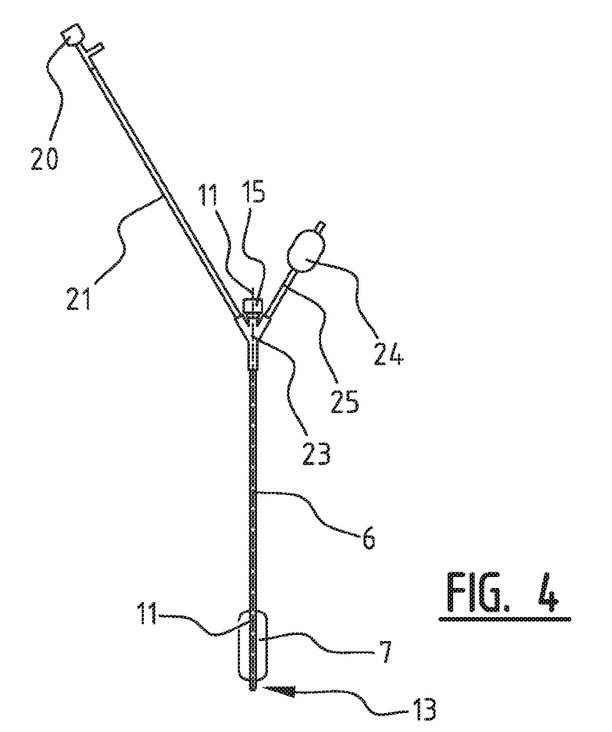
FIG. 4 is a schematic view of another exemplary embodiment of the system of the invention, including a full length stylet, showing the elastically expandable balloon connected to the inflatable member filled with fluid.
Figure 5:
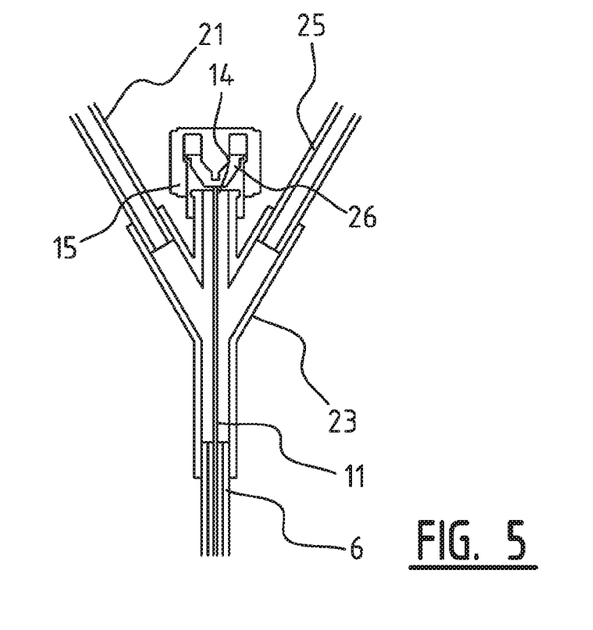
FIG. 5 is a detailed, enlarged scale view of the encircled area III in FIG. 4.

In another exemplary embodiment the stylet 11 extends over the entire length of the flexible catheter 6 (FIGS. 4 and 5). A distal end 12 of the stylet 11 extends beyond the inflatable member 7 to a distal end 13 of the catheter 6. A proximal end 14 of the stylet 11 protrudes from the proximal end of the catheter 6 outside the patient's body and extends through the centre prong of a trident connector 23 (FIG. 5). This centre prong is closed by a cap 15 carrying a valve member 26, the function of which will be described below. This arrangement allows the inflatable member 7 to be swiftly and accurately positioned in the respiratory tract 3, since the presence of the stylet 11 adds stiffness to the flexible catheter 6, thus improving directional control and predictability of the movement. To allow the stylet 11 to be retracted after the inflatable member 7 has been filled with the fluid, without the risk of fluid leaking from the system, the proximal end 14 of the stylet 11 protrudes from the catheter 6 through a valve member 26. In the illustrated embodiment this valve member 26 is a one-way valve that is arranged in the centre prong of the trident connector 23.

Figure 6:
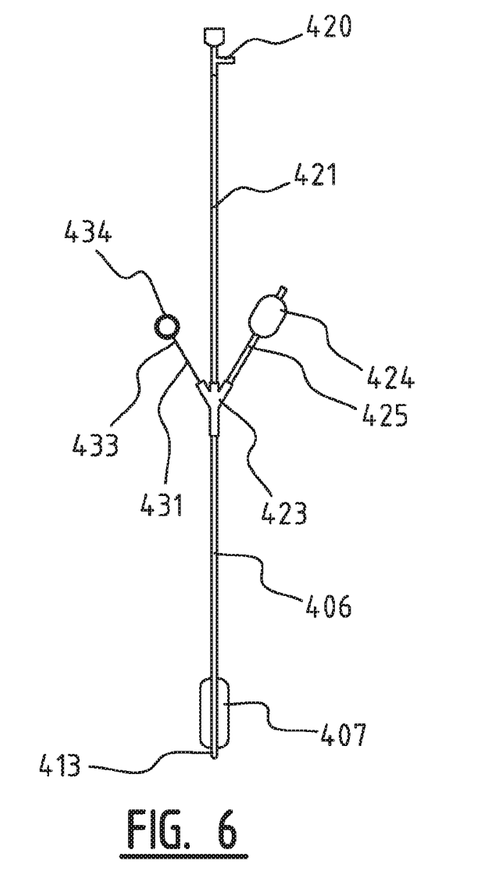
FIG. 6 is a schematic view of an exemplary embodiment of an ultrasonic imaging system of the invention, including a pull wire.
Figure 7:
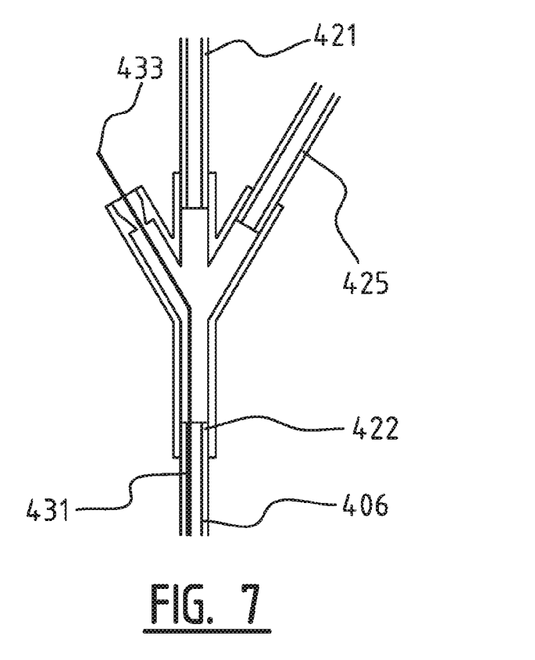
FIG. 7 is a detailed, enlarged scale view of the encircled area X in FIG. 6.

In a further embodiment of the invention which is illustrated in FIGS. 6 and 7 the guide means comprise a wire 431 rather than a stylet. A distal end 432 of the wire 431 is eccentrically connected to the flexible catheter 406 and a proximal end 433 of the wire 431 is connected to a pulling member 434 arranged outside the patient's body 1 (FIG. 6). The wire 431, which is very thin, provides excellent guidance of the catheter 406 with minimum obstruction of the image. The inflatable member 407 is positioned in the respiratory tract by manipulating the pulling member 434. By pulling on the wire 431, its effective length within the catheter 406 will decrease. Since the wire 431 is eccentrically attached to the catheter 406, shortening of the wire 431 will lead to the catheter 406 assuming a curved shape, at least in the vicinity of the point where the wire 431 is attached. In the illustrated embodiment this attachment point is located near the distal end 413 of the catheter 406. This location allows optimum control of the catheter 406.

In this embodiment the inflatable member 407 is again filled by means of a syringe which may be connected to a fill connector 420 at the end of a fill line 421. This fill line 421 is again connected to the catheter 406 through a trident connector 423, in this case through the centre prong thereof. Also connected to the trident connector 423 is a pilot line 425 carrying an elastically expandable balloon 424. Finally, the proximal end of the wire 431 is guided through the third prong of the trident connector 423. In order to prevent fluid leakage, the proximal end 433 of the pull wire 431 protrudes from this third prong through a valve member, in particular a one-way valve 426 (FIG. 7).

Figure 8:
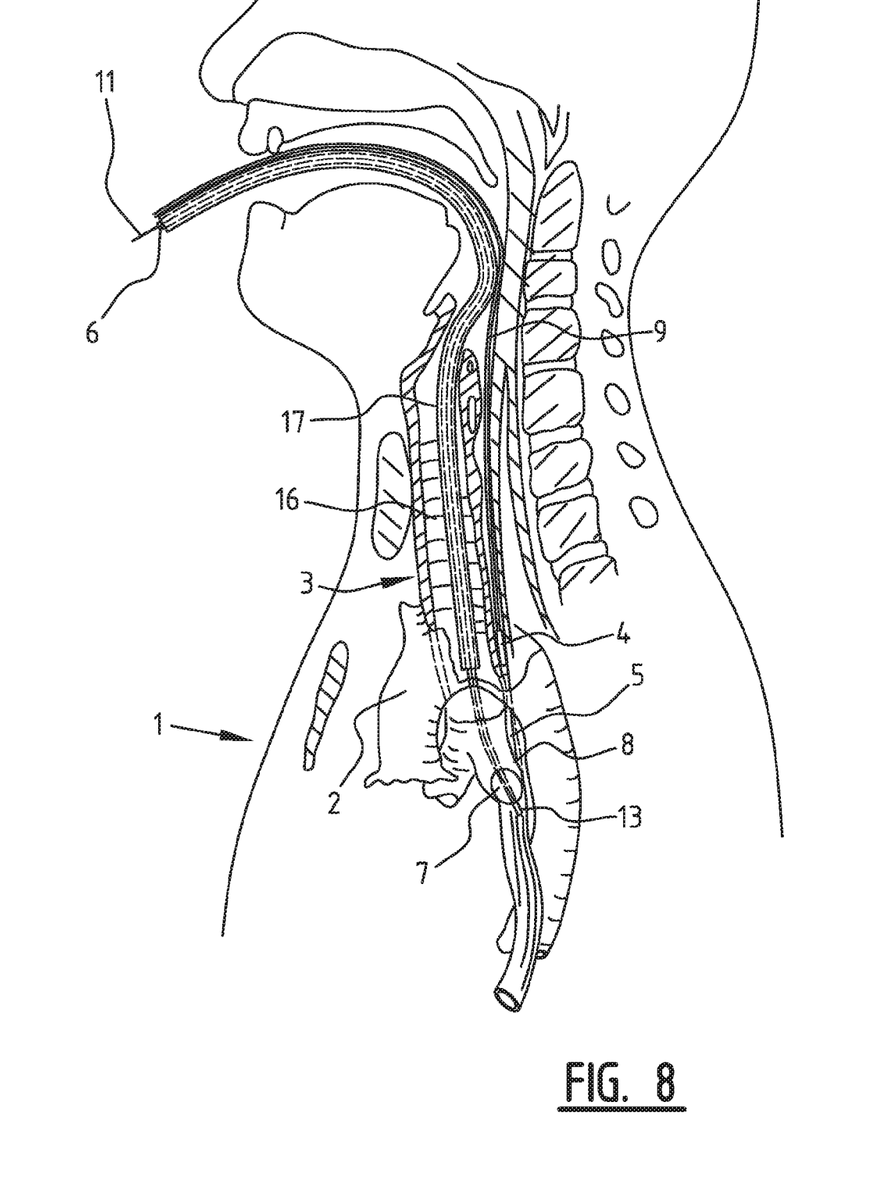
FIG. 8 is a partial sectional view of a patient's upper body showing the ultrasonic imaging system of the invention during visualization of an organ.

In a preferred exemplary embodiment illustrated in FIG. 8 the system comprises an ultrasonic imaging device, which enables the imaging of an organ in a patient's body 1, in particular the heart or the aorta 2, through a part of the patient's respiratory tract 3. First an ultrasonic imaging device 4, for instance an echo probe, is arranged in or on the patient's body 1. In the shown embodiment, the echo probe 4, which is carried on a flexible catheter 9, is introduced into the patient's oesophagus 5 (FIG. 8). Then another flexible catheter 6 carrying an inflatable member 7 is introduced into the respiratory tract 3. The inflatable member 7 is positioned at a predetermined location in the respiratory tract 3. When the organ to be imaged is the ascending aorta 2, the predetermined position will be in the top part of the left bronchus 8. The flexible catheter 6 carrying the inflatable member 7 will be guided through the patient's trachea 16 by first introducing an endotracheal tube 17 into the trachea 16. This tube 17 is somewhat stiffer than the catheter 6 and therefore easier to control. The catheter 6 is then inserted in the endotracheal tube 17. After leaving the endotracheal tube 17 the distal end 13 of the catheter 6 and the inflatable member 7 are guided into the left bronchus 8.

Figure 9:
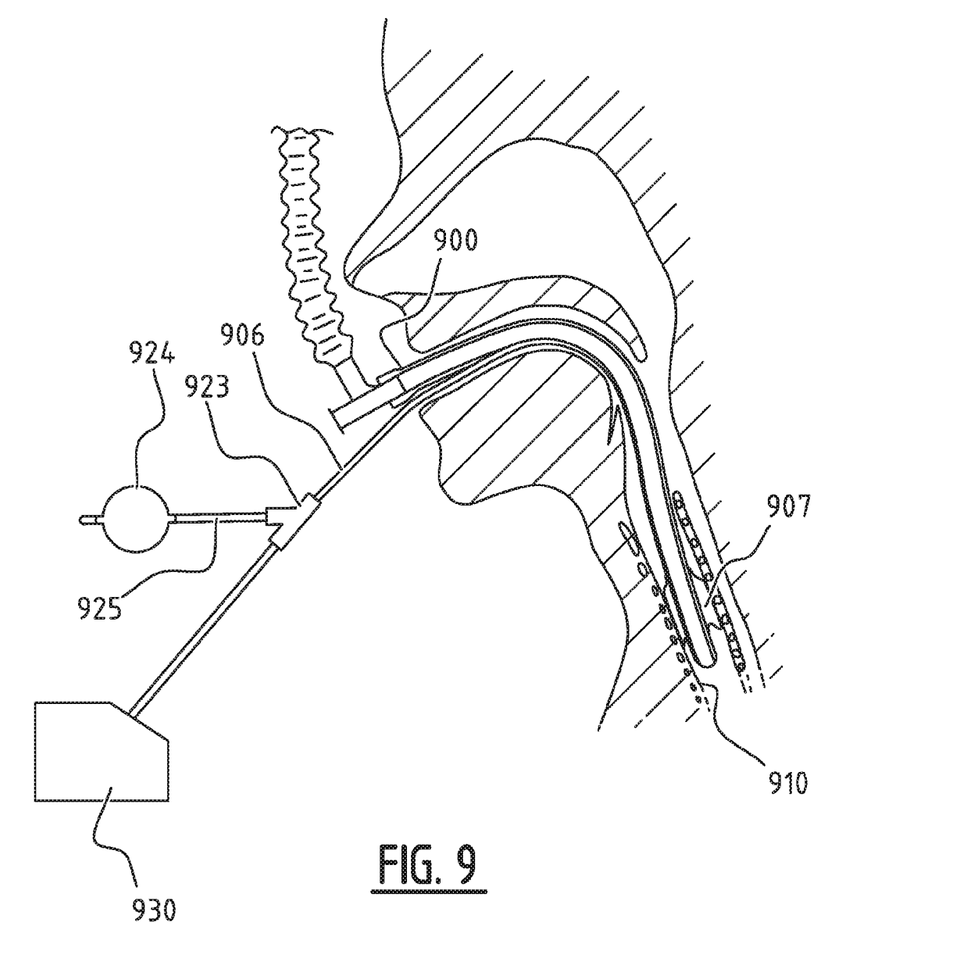
FIG. 9 is a partial sectional view of another exemplary embodiment of a system of the invention including a tracheal breathing tube in place within a trachea and surrounded by an inflatable member connected to a pressure monitoring and control member.

In another exemplary embodiment illustrated in FIG. 9 the system comprises a trachea breathing tube 900 which enables mechanical ventilation without aspiration of secretion, for instant, during anaesthesia of the patient. The proximal end of the breathing tube 900 is adapted for connection to a source of respiratory gas. The distal end of the breathing tube 900 which is located within the trachea 910 is surrounded by an inflatable member 907 which is connected via a flexible catheter 906 to a connector 923. The connector 923 provides fluid communication between the catheter 906 and an elastically expandable balloon 924 located externally of the patient's body. The expandable balloon 924 is connected to the connector 923 via a fluid line 925. The connector 923 is further connected to a fluid source 930, e.g. a syringe, outside the patient's body, for filling the inflatable member 907 with a fluid. When the breathing tube 900 is in place within the trachea 910, the inflatable member 907 is inflated to an extent so as to form a seal against the wall of the trachea and prevent aspiration of fluid in either direction along the trachea. An elastically expandable balloon 924 is provided at the one of the outer ends of the catheter 906 as a visual indication of the approximate pressure in the inflatable member 907, as well as a controller for sudden pressure increase in the inflatable member 907. In case of excessive pressure increase exceeding the predetermined threshold pressure within the inflatable member 907, e.g. because of the movement of breathing tube 910 or spontaneous breathing, the elastically expandable balloon 924 may expand to limit the pressure increase within the inflatable member 907 to a safety level, thereby causing no damage to the respiratory tract wall.

Thus, embodiments of the invention provide a system with which an inflatable member that is to be filled with a fluid may be positioned at a predetermined position within the respiratory tract of a patient, which allows for an improved pressure control aimed at avoiding damage to the respiratory tract wall. This in turn allows a safer procedure for e.g. the ultrasonic imaging of certain parts of the circulatory system, in particular the heart or aorta, using an imaging device that is arranged in the patient's oesophagus, as well as for mechanical ventilation using a breathing tube during anaesthesia.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system with at least one inflatable member configured for being arranged in a part of a patient's respiratory tract, the system comprising:
    a catheter carrying the at least one inflatable member, said catheter comprising a fluid line for filling the inflatable member with a fluid; and
    a pressure monitoring and control member to be arranged outside the patient's body, said pressure monitoring member being in fluid communication with the inflatable member and being configured to receive, during operation, fluid from the inflatable member when a pressure increases above a predetermined threshold pressure and to return said received fluid when the pressure decreases below said predetermined threshold pressure;
    wherein the pressure monitoring and control member is an elastically expandable balloon made from a material configured to expand elastically when a pressure in the balloon increases above a predetermined threshold pressure and to contract when the pressure in the balloon decreases below said predetermined threshold pressure.

2. The system of claim 1, further comprising an imaging device configured to be arranged in or on the patient's body; wherein said fluid is an imaging liquid.

3. The system of claim 1, further comprising a trachea tube having a first end and a second end, wherein said first end is adapted for connection to a source of respiratory gas, and said second end is adjacent to and attached around by the inflatable member.

4. The system of claim 1, wherein the volume of the elastically expandable balloon, in a non-expanded state, is at least 10 percent of the volume of the inflatable member.

5. The system of claim 1, wherein the material of the elastically expandable balloon is a thermoplastic elastomer.

6. The system of claim 1, wherein the durometer hardness of the material of the elastically expandable balloon, using test method of ASTM D2240, is lower than the durometer hardness of the material of the inflatable member.

7. The system of claim 1, wherein the tensile modulus of the material of the elastically expandable balloon, using the test method of ASTM D412, is lower than the tensile modulus of the material of the inflatable member.

8. The system of claim 1, wherein the predetermined threshold pressure lies in a range between 30 and 70 mm Hg.

9. The system of claim 1, wherein the volume of the elastically expandable balloon, in the non-expanded state, is between 2 and 10 ml.

10. The system of claim 1, wherein the expansion of the expandable balloon, when the pressure is above the predetermined threshold pressure, is essentially linear with respect to the pressure.

11. The system of claim 1, wherein the material of the inflatable member is a thermoplastic elastomer.

12. The system of claim 1, wherein the inflatable member, in the non-expanded state, has a volume between 20 ml and 60 ml.

13. The system of claim 1, further comprising positioning means for positioning the inflatable member at a predetermined location in the respiratory tract.

14. The system of claim 13, wherein the positioning means comprise guide means attached to or integrated with the flexible catheter.

15. The system of claim 14, wherein the guide means comprise a stylet arranged in the catheter and having a distal end at a tip of the catheter, said stylet extending beyond the inflatable member.

16. The system of claim 1, wherein the elastically expandable balloon has a thickness between 0.01 mm and 0.1 mm.

17. A system with at least one inflatable member configured for being arranged in a part of the patient's respiratory tract, the system comprising:
   a catheter carrying the at least one inflatable member, said catheter comprising a fluid line for filling the inflatable member with a fluid;
   a pressure monitoring and control member to be arranged outside the patient's body, said pressure monitoring and control member being in fluid communication with the inflatable member and being configured to receive, during operation, fluid from the inflatable member when a pressure increases above a predetermined threshold pressure and to return said received fluid when the pressure decreases below said predetermined threshold pressure; and
   an ultrasonic imaging device, configured to be arranged in or on the patient's body;
   wherein said fluid is an imaging liquid;
   wherein the pressure monitoring and control member is an elastically expandable balloon made from a material configured to expand elastically when a pressure in the balloon increases above a predetermined threshold pressure and to contract when the pressure in the balloon decreases below said predetermined threshold pressure;
   wherein the volume of the elastically expandable balloon, in a non-expanded state, is at least 10 percent of the volume of the inflatable member.

18. The system of claim 17, wherein the material of the elastically expandable balloon is a thermoplastic elastomer.

19. A system with at least one inflatable member configured for being arranged in a part of the patient's respiratory tract, the system comprising:
   a catheter carrying the at least one inflatable member, said catheter comprising a fluid line for filling the inflatable member with a fluid;
   a pressure monitoring and control member to be arranged outside the patient's body, said pressure monitoring and control member being in fluid communication with the inflatable member and being configured to receive, during operation, fluid from the inflatable member when a pressure increases above a predetermined threshold pressure and to return said received fluid when the pressure decreases below said predetermined threshold pressure;
   wherein the pressure monitoring and control member is an elastically expandable balloon made from a material configured to expand elastically when a pressure in the balloon increases above a predetermined threshold pressure and to contract when the pressure in the balloon decreases below said predetermined threshold pressure;
   wherein the volume of the elastically expandable balloon, in the non-expanded state, is between 2 and 10 ml;
   wherein the inflatable member, in a non-expanded state, has a volume between 20 ml and 60 ml.

20. The system of claim 19, further comprising an imaging device configured to be arranged in or on the patient's body; wherein said fluid is an imaging liquid.

* * * * *